United States Patent

Winkel et al.

Patent Number: 4,744,828
Date of Patent: May 17, 1988

[54] (METH)-ACRYLIC ACID ESTERS AND THE USE THEREOF

[75] Inventors: Jens Winkel, Cologne; Bruno Bömer, Bergisch-Gladbach; Carlhans Süling, Odenthal; Jürgen Reiners, Leverkusen; Wolfgang Podszun, Cologne, all of Fed. Rep. of Germany

[73] Assignee: Bayer Aktiengesellschaft, Leverkusen, Fed. Rep. of Germany

[21] Appl. No.: 870,610

[22] Filed: Jun. 4, 1986

[30] Foreign Application Priority Data

Jun. 20, 1985 [DE] Fed. Rep. of Germany ....... 3522005

[51] Int. Cl.$^4$ .................. A61K 6/02; C07C 69/52; C07C 125/06
[52] U.S. Cl. .................. 106/35; 260/998.11; 433/217.1; 433/226; 560/115; 560/160; 560/220
[58] Field of Search .............. 560/115, 160, 220; 106/35; 433/226, 217.1; 260/998.11

[56] References Cited

U.S. PATENT DOCUMENTS

| | | | |
|---|---|---|---|
| 4,131,729 | 12/1978 | Schmitt et al. | 526/282 |
| 4,172,951 | 10/1979 | Gruber et al. | 560/194 |
| 4,323,348 | 4/1982 | Schmitz-Josten et al. | 106/35 |
| 4,323,696 | 4/1982 | Schmitz-Josten et al. | 560/220 |
| 4,347,174 | 8/1982 | Nagase et al. | 260/998.11 |
| 4,379,695 | 4/1983 | Orlowski et al. | 433/217.1 |
| 4,383,826 | 5/1983 | Butler et al. | 106/35 |
| 4,420,306 | 12/1983 | Orlowski et al. | 106/35 |
| 4,605,719 | 8/1986 | Peelen | 526/282 |

FOREIGN PATENT DOCUMENTS

| | | |
|---|---|---|
| 2816823 | 10/1978 | Fed. Rep. of Germany . |
| 2931926 | 2/1981 | Fed. Rep. of Germany . |
| 3135115 | 3/1983 | Fed. Rep. of Germany . |
| 3338077 | 5/1985 | Fed. Rep. of Germany . |

OTHER PUBLICATIONS

Progress in Organic Coatings, 11(1983) 297–308, Silane Adhesion Promoters in Coatings, Edwin P. Plueddemann.
Initiator–Accelerator Systems for Dental Resins, G. M. Brauer and H. Argentar, National Bureau of Standards, Washington, D.C. 20234 pp. 360–371.

Primary Examiner—Paul Lieberman
Assistant Examiner—Linda D. Skaling
Attorney, Agent, or Firm—Sprung Horn Kramer & Woods

[57] ABSTRACT

The invention relates to novel (meth)-acrylic acid derivatives of tricyclodecanes of the formula

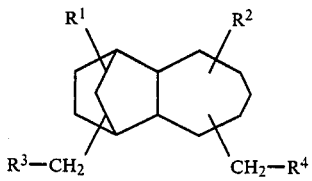

in which $R^1$ and $R^2$ are identical or different and denote hydrogen, lower alkyl, lower alkoxy, halogen or trifluoromethyl and $R^3$ and $R^4$ are identical or different and represent the groups.

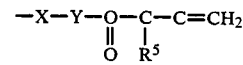

in which
X is a divalent bridge member comprising the group

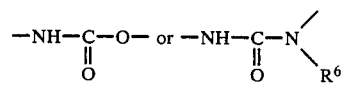

and
Y is a linear or branched hydrocarbon chain which has 2 to 10 carbon atoms and can optionally contain oxygen bridges and is optionally substituted by 1 to 4 acrylate or methacrylate radicals, and
$R^5$ represent hydrogen or methyl and
$R^6$ represents hydrogen, lower alkyl or phenyl
and to their use in dental compositions.

9 Claims, No Drawings

(METH)-ACRYLIC ACID ESTERS AND THE USE THEREOF

The invention relates to new acrylic acid and methacrylic acid derivatives, described in the following text as (meth)-acrylic acid derivatives, of tricyclodecanes, and to the preparation thereof. The new compounds can be employed as monomers for use in the dental field.

Dental compositions containing polymerisable (meth)-acrylic acid esters of tricyclodecanes have been disclosed in German Offenlegungsschrift No. 2,931,926. When used, however, these dental compositions still exhibit an undesirable shrinkage on polymerisation.

New (meth)-acrylic acid derivatives of tricyclodecanes of the formula

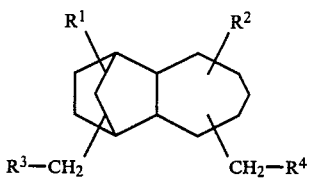

in which
$R^1$ and $R^2$ are identical or different and denote hydrogen, lower alkyl, lower alkoxy, halogen or trifluoromethyl and
$R^3 R^4$ are identical or different and represent the groups

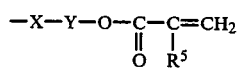

in which
X is a divalent bridge member comprising the group

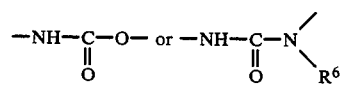

and
Y is a linear or branched hydrocarbon chain which has 2 to 10 carbon atoms and can optionally contain oxygen bridges and is optionally substituted by 1 to 4 acrylate or methacrylate radicals, and
$R^5$ represents hydrogen or methyl and
$R^6$ represents hydrogen, lower alkyl or phenyl, have been found.

Dental compositions in which the (meth)-acrylic acid derivatives of tricyclodecanes, according to the invention, are used as the starting materials exhibit, surprisingly, a substantially smaller shrinkage on polymerisation and are therefore particularly suitable for use in practice.

Within the scope of the present invention, the substituents can have the following meaning:

Lower alkyl can denote a linear or branched hydrocarbon radical having 1 to about 6 carbon atoms. The following lower alkyl radicals may be mentioned as examples: methyl, ethyl, propyl, isopropyl, butyl, tert. butyl, isobutyl, pentyl, isopentyl, hexyl and isohexyl. The methyl radical and the ethyl radical are preferred.

Lower alkoxy can denote a linear or branched hydrocarbon radical which has 1 to about 6 carbon atoms and is attached via oxygen. The following lower alkoxy radicals may be mentioned as examples: methoxy, ethoxy, propoxy, isopropoxy, butoxy, isobutoxy, pentoxy, isopentoxy, hexoxy and isohexoxy. The methoxy radical and the ethoxy radical are preferred.

Halogen can denote fluorine, chlorine, bromine or iodine. Preferred halogens are fluorine and chlorine.

Y is, in general, a linear or branched hydrocarbon chain which has 2 to 10 carbon atoms and is optionally substituted by 1 to 4 methacrylate or acrylate radicals. The hydrocarbon chain can optionally contain 1 to 3, preferably 1 to 2, oxygen groups. The following meanings of Y may be mentioned as examples: ethylene, propylene, 2-(meth)-acryloyloxy-1,3-propylene, 3-(meth)-acryloyloxy-1,2-propylene, 2-(meth)-acryloyloxymethyl-2-ethyl-1,3-propylene and 2,2-bis-(meth)-acryloyloxymethyl-1,3-propylene.

Preferred (meth)-acrylic acid derivatives of tricyclodecanes according to formula I are those in which $R^1$ and $R^2$ denote hydrogen, $R^3$ and $R^4$ are identical or different and represent the group

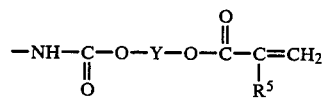

in which
Y is a linear or branched hydrocarbon chain which has 2 to 10 carbon atoms and which can optionally contain 1 to 3 oxygen bridges and can optionally be substituted by 1 to 4 acrylate or methacrylate radicals, and
$R^5$ represents hydrogen or methyl.

The substituents $R^3$ and $R^4$ are alkoxycarbonylamino radicals which contain methacrylate groups and which can be obtained, for example, by reacting appropriate isocyanate groups with hydroxy compounds containing methacrylate groups. Hydroxyethyl (meth)-acrylates, 2-hydroxypropyl (meth)-acrylates, trimethylolpropane di-(meth)-acrylates, propanetriol di-(meth)-acrylates and pentaerythritol tri-(meth)-acrylates and dipentaerythritol penta-(meth)-acrylates, for example, are preferred. Hydroxy compounds containing both acrylate and methacrylate groups are also very suitable. Hydroxy compounds which are particularly preferred are 2-hydroxypropyl methacrylate and propanediol methacrylate (mixture of the 1,2-methacrylate and the 1,3-methacrylate) of hydroxy-methacryloyloxy-acryloyloxypropane (mixture of the 1,2-diester and 1,3-diester).

The following (meth)-acrylic acid derivatives of tricyclodecanes may be mentioned as examples:

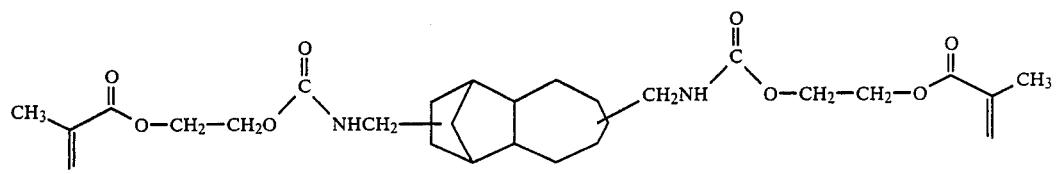
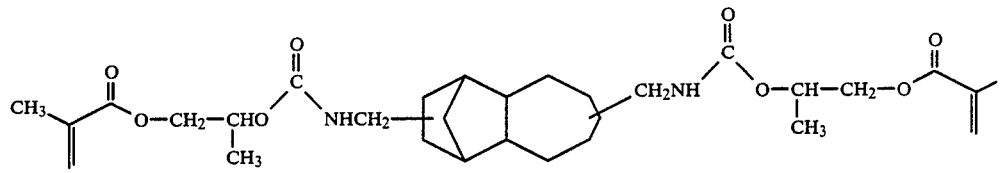
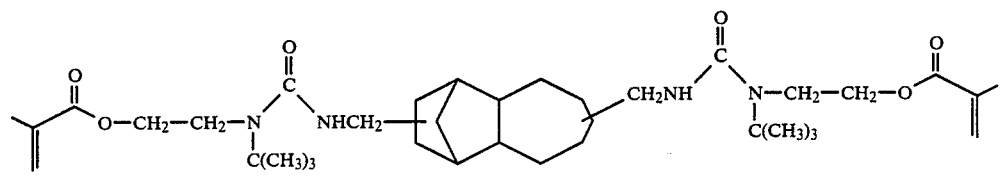
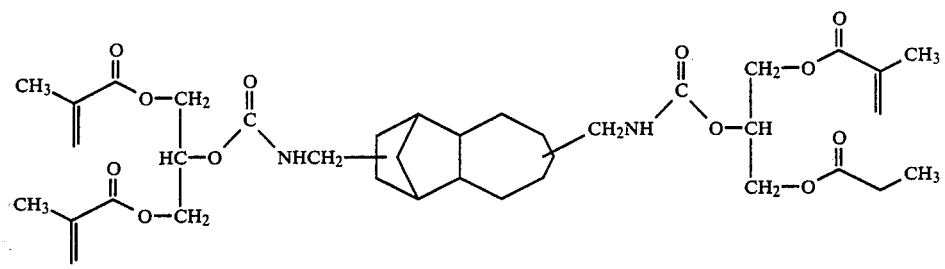
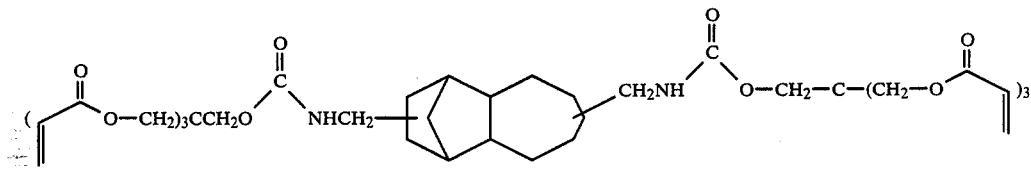
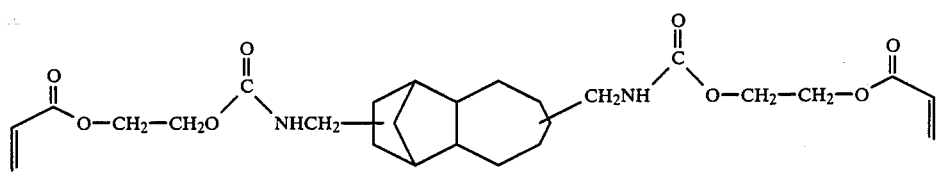
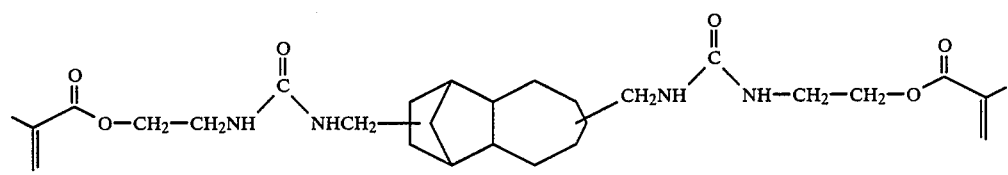
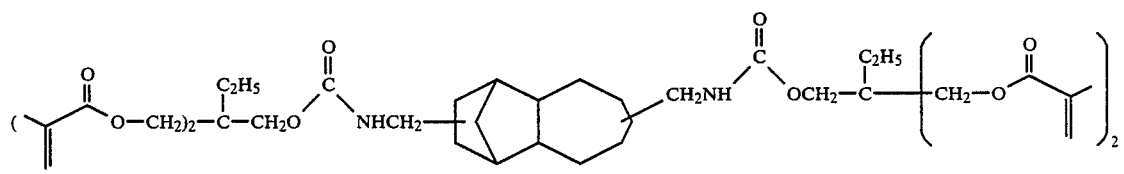
A process has also been found for the preparation of the (meth)-acrylic acid derivatives of tricyclodecanes according to the invention, which process is characterised in that diisocyanatomethyltricyclodecanes of the formula

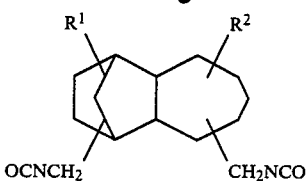

(II)

in which R¹ and R² are identical or different and denote hydrogen, lower alkyl, lower alkoxy, halogen or trifluoromethyl,
are reacted, if appropriate in an inert solvent, in the presence of a catalyst within the temperature range from 0° to 100° C., with (meth)-acrylic acid derivatives of the formulae

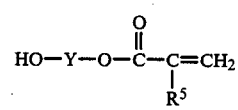

(III)

or

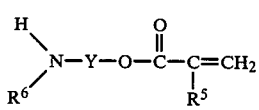

(IV)

in which
Y is a linear or branched hydrocarbon chain which has 2 to 10 carbon atoms and which can optionally contain oxygen bridges and is optionally substituted by 1 to 4 acrylate or methacrylate radicals, and
$R^5$ represents hydrogen or methyl.

Diisocyanatomethyltricyclodecanes are in themselves known and can be prepared, for example, by reacting a diaminomethyltricyclodecane with phosgene.

(Meth)-acrylic acid derivatives of the formula (III) are in themselves known (German Pat. No. 3,234,045) and can be prepared, for example, by reacting epoxides with (meth)-acrylic acid.

(Meth)-acrylic acid derivatives of the formula (IV) are in themselves known (German Auslegeschrift No. 1,235,896) and can be prepared, for example, by reacting alkanolamines with acid halides.

It is possible to carry out the process according to the invention in the absence of a solvent. Inert solvents for the process according to the invention are preferably non-polar solvents which are unaffected under the reaction conditions. The following solvents are particularly preferred: chloroform, tetrahydrofuran, dioxane, methylene chloride, toluene, acetonitrile and freon. Chloroform, tetrahydrofuran, freon and acetonitrile are particularly preferred.

In a particular embodiment, the process according to the invention is carried out with the exclusion of water. A maximum amount of less than 0.1% of water is particularly preferred.

Catalysts for the process according to the invention are, in general, metal salts of higher fatty acids. Examples of preferred catalysts are dibutyltin laurate or tin-(II) octoate. However, compounds having tertiary amino groups, such as pyridine, methylpyridine, N,N'-dimethylpiperazine, N,N-dimethylbenzylamine and others, and titanium compounds are also preferred.

In general, the catalyst is employed in an amount of 0.1 to 2.5% by weight, preferably 0.1 to 1.5% by weight, relative to the total amount of the reactants.

In a preferred embodiment, the process according to the invention can be carried out in the presence of a polymerisation inhibitor. Examples of polymerisation inhibitors for this purpose can be known compounds (from Ullmanns Encyklopädie der technischen Chemie (Ullmann's Encyclopedia of Industrial Chemistry"), 4th edition, Verlag Chemie, Weinheim, volume 8, pages 19–45). 2,6-Ditert.-butyl-4-methylphenol may be mentioned as an example. The oxygen of the air which is introduced into the reaction mixture is also an example of a preferred polymerisation inhibitor.

In general, the polymerisation inhibitor is employed in an amount of 0.01 to 0.2% by weight, preferably 0.1 to 0.05% by weight.

The process according to the invention is generally carried out within the temperature range from 0° to 100° C., preferably from 30° to 70° C. The process according to the invention is generally carried out under normal pressure. However, it is also possible to carry out the process according to the invention under a reduced or elevated pressure (for example within the pressure range from 0.1 to 10 bar).

The process according to the invention can, for example, be carried out as follows:

The reactants are dissolved in the solvent, and the catalyst and, if appropriate, the polymerisation inhibitor, are added, with stirring. The progress of the reaction against time can, for example, be followed by determining the IR spectra. When the isocyanate groups have reacted completely, the reaction products are isolated by removing the solvent. Previous purification by means of adsorbents, or active charcoal, bleaching earth, silica gel or aluminium oxide is possible.

The (meth)-acrylic acid derivatives of tricyclodecanes according to the invention can be used as monomers for dental materials. It is possible to employ them in the dental field as monomers for polymeric tooth-filling compositions or coating agents (dental varnishes).

For use as monomers for polymeric tooth-filling compositions or coating agents in the dental field, the (meth)-acrylic acid derivatives of tricyclodecanes according to the invention can be mixed with monomers which are in themselves known in order, for example, to adjust the viscosity to suit the intended use. Viscosities within the range from 60 to 10,000 mPas are preferred in this connection. This range can be achieved by mixing into the monomers according to the invention, if appropriate, a comonomer of low viscosity as a reactive thinner. The compounds according to the invention are employed in the mixture with comonomers in a proportion of approx. 30 to approx. 90% by weight, preferably 50 to 80% by weight. The purpose of the present invention is to employ, with similar preference, mixtures of various (meth)-acrylic acids according to the invention.

It is also possible to employ mixtures of monomers containing several comonomers as reactive thinners.

The following comonomers may be mentioned as examples: glycerol dimethacrylate, triethylene glycol dimetharcylate, tetraethylene glycol dimethacrylate, 1,12-dodecanediol dimethacrylate, 1,6-hexanediol dimethacrylate, diethylene glycol dimethacrylate, 2,2-bis-[p-(2'-hydroxy-3'-methacryloyloxypropoxy)-phenyl]-propane, 2,2-bis-[2'-methacryloyloxyethoxy)-phenyl]-propane, trimethylolpropane tri-(meth)-acrylate and bis-(meth)acryloyloxyethoxymethyltricyclo-[5.2.1.0$^{2.6}$]-decane (German Offenlegungsschrift No. 2,931,925 and German Offenlegungsschrift No. 2,931,926).

Comonomers having a boiling point above 100° C. at 13 mbar are particularly preferred.

The (meth)-acrylic acid esters according to the invention, if appropriate as mixtures with the comonomers mentioned, can be cured by methods which are in themselves known to give crosslinking polymers (Am. Chem. Soc., Symp. Ser. 212, 359–371 (1983)). A system composed of a peroxide compound and a reducing agent, for example one based on tertiary aromatic amines, is suitable for redox polymerisation, as it is called. The following are examples of peroxides: dibenzoyl peroxide, dilauroyl peroxide and di-4-chlorobenzoyl peroxide.

Examples of tertiary aromatic amines which may be mentioned are N,N-dimethyl-p-toluidine, bis-(2-hydroxyethyl)-p-toluidine, bis-(2-hydroxyethyl)-3,5-dimethylaniline and N-methyl-N-(2-methylcarbamoyloxypropyl)-3,5-dimethylaniline. It is advantageous to select the concentration of the peroxide or amine so that it amounts to 0.1 to 5% by weight, preferably 0.5 to 3% by weight, relative to the monomer mixture. The monomer mixtures containing peroxides or amines, respectively, are stored separately until they are used.

The monomers according to the invention can also be induced to polymerise by irradiation with UV light or visible light (for example within the wavelength range from 230 to 650 nm). Examples of suitable initiators for the photo-initiated polymerisation are benzil, benzil dimethyl ketal, benzoin monoalkyl ethers, benzophenone, p-methoxybenzophenone, fluorenone, thioxanthone, phenantrhenequinone and 2,3-bornanedione (camphor quinone), if appropriate in the presence of activators having a synergistic action, such as N,N-dimethylaminoethyl methacrylate, triethanolamine or 4-N,N-dimethylaminobenzenesulphonic acid diallylamide. The procedure for the photopolymerisation is described, for example, in German Patent Specification No. 3,135,115.

In addition to the initiators described above, it is possible to add, to the (meth)-acrylic acid derivatives according to the invention, light stabilisers and stabilisers which are in themselves known for this intended use.

Light stabilisers are described, for example, in (Gächter, Müller, Taschenbuch der Kunststoff-Additive ("Manual of Additives for Plastics"), 2nd edition, Carl Hauser Verlag). The following light stabilisers may be mentioned as examples: Cyasorb UV9 ®, Tinuvin P ®, Tinuvin 770 ®, Tinuvin 622 ® and Tinuvin 765 ®.

Stabilisers are described, for example, in ("Ullmanns Encyklopädie der technischen Chemie (Ullmann's Encyclopedia of Industrial Chemistry"), 4th Edition, volume 8). The following stabilisers may be mentioned as examples: 2,6-ditert.-butylphenol, 2,6-ditert.-butyl-4-methylphenol, 2,6-dioctadecyl-4-methylphenol, 1,1'-methylenebis-(2-naphthol) and others.

The light stabilisers and the stabilisers can each be employed in an amount of 0.01 to 0.5 parts by weight, relative to 100 parts by weight of the monomer mixture. The monomer mixtures can be employed as coating agents (dental varnishes) without the addition of fillers.

Fillers are generally added to the resulting monomer mixtures when they are used as tooth filling compositions. Monomer mixtures having a high viscosity within the range from 60 to 10,000 mPas are particularly advantageous in order to enable a high degree of filling to be achieved.

It is advantageous to mix inorganic fillers to the (meth)-acrylic acid derivatives of tricyclodecanes according to the invention. Examples which may be mentioned are rock crystal, graphite, cristobalite, quartz glass, highly diperse silica, aluminium oxide and glass ceramics, for example glass ceramics containing Lanthanum and zirconium (German Offenlegungsschrift No. 23,740,501). In order to improve the bond to the polymer matrix of the polymethacrylate, it is preferable to pretreat the inorganic fillers with an adhesion promoter. The promotion of adhesion can be achieved, for example, by treatment with organosilicon compounds (Progress in Organic Coatings 11, 297–308 (1983)). It is preferable to employ 3-methacryloyloxypropyltrimethoxysilane. In general, the fillers for the tooth-filling compositions according to the invention have an average particle diameter of 0.01 to 100 μm, preferably 0.05 to 50 μm, particularly preferably 0.05 to 5 μm. It can also be advantageous to employ simultaneously several fillers differing from one another in particle diameter.

In general, the proportion of filler in the tooth-filling composition is 5 to 85% by weight, preferably 50 to 80% by weight.

The components are used for the preparation of the tooth-filling compositions by using commercially available kneading machines.

The proportion of the (meth)-acrylic acid derivatives of tricyclodecanes according to the invention in the filling compositions is generally 5 to 85% by weight, relative to the filling composition.

Surprisingly, the dental varnishes and tooth-filling compositions according to the invention have a particularly low shrinkage on polymerisation and a good capacity for mechanical uses.

PREPARATION EXAMPLES

1. Reaction of 3(4),8(9)-diisocyanatomethyltricyclo-(5.2.1.0$^{2,6}$)-decane with hydroxyethyl methacrylate 0.8 mol of hydroxyethyl methacrylate, 0.4 mol of diisocyanate, 0.13 g of 2,6-ditert.-butyl-4-methylphenol (ionol) and 0.5 g of dibutyltin dilaurate are reacted at 50° C. for 6 hours in a suitably equipped reaction vessel, with stirring and with dry air blown through the mixture.

| Found | Calculated |
|---|---|
| % C 61.8 | % C 61.7 |
| % H 7.2 | % H 7.5 |
| % N 5.4 | % N 5.5 |

Molecular weight (by osmometry): 500–511 (calculated 506)

2. Reaction of 3(4),8(9)-diisocyanatomethyltricyclo-(5.2.1.0$^{2,6}$)-decane with hydroxypropyl methacrylate 0.8 mol of propyl 2-hydroxy methacrylate, 0.4 mol of diisocyanate, 0.13 g of ionol and 0.15 g of dibutyltin dilaurate are reacted as described in (1).

| Found | Calculated |
|---|---|
| % C 62.6 | % C 62.9 |
| % H 5.2 | % H 5.2 |
| % N 8.1 | % N 7.9 |

Molecular weight (by osmometry): 527 (calculated 534)
viscosity (25° C.): 356,000 mPas.

3. Reaction of 3(4),8(9)-diisocyanatomethyltricyclo-(5.2.1.0$^{2,6}$)-decane with N-t-butylaminoethyl methacrylate 0.7 mol of N-t-butylaminoethyl methacrylate is initially placed in a suitably equipped reaction vessel, and 0.35 mol of diisocyanate is added slowly, with stirring and with dry air passed through the mixture. After the addition is complete, the reaction mixture is stirred for a further 30 minutes.

4. Reaction of 3(4),8(9)-diisocyanatomethyltricyclo-(5.2.1.0$^{2,6}$)-decane with glycerol dimethacrylate 114 g of glycerol dimethacrylate, 0.5 g of dibutyltin dilaurate and 0.063 g of ionol are dissolved in 200 ml of methylene chloride in a suitably equipped reaction vessel. 615 g of diisocyanate are added dropwise to this solution at room temperature. The reaction mixture is then stirred at 40°–50° C. for 50 hours. A clear, colourless liquid is obtained after the solvent has been removed by distillation on a rotary evaporator.

IR (cm$^{-1}$): 3380 (N—H); 1725 (C=O); 1715 (C=O); 1160 (C—O).

H-NMR (ppm) in CDCl$_3$/TMS: 6.16, 5.62 (=CH$_2$, 8H); 5.1–5.5 (=CH$_3$—4H); 4.2–4.5 (COO—CH$_2$—, 8H), 3.0 (—CONH—CH$_2$—, 4H), 1.95, 2.5–2.0, 1.7–1 (CH$_3$, TCD—CH$_2$, 26H).

| Found | Calculated |
|---|---|
| % C 66.3 | % C 66.2 |
| % H 8.6 | % H 9.1 |
| % N 9.0 | % N 9.1 |

Molecular weight (by osmometry): 627 (calculated 616)
viscosity (25° C.): 1,220,000 mPas.

Use examples

5. Measurement of shrinkage on polymerisation

2% of benzoyl peroxide are dissolved in pure monomer. 5 g of this solution are put into a cylindrical glass vessel of diameter 3 cm and are blanketed with nitrogen. The solutions are heated at 80° C. for 1 hour and at 130° C. for 15 minutes, in the course of which the monomers polymerise. The density of the resulting samples is determined, and the shrinkage on polymerisation is determined by comparing their density with that of the liquid monomers.

TABLE I

| Monomer for comparison tests | Shrinkage on polymerisation |
|---|---|
| (German Offenlegungsschrift 2,931,926) | 7.3% |
| (German Offenlegungsschrift 2,816,823) | 7.7% |
| Monomers according to the invention | |
| | 6.0% |
| | 6.3% |

6. Composition for filling dental cavities (a) Redox-curving system peroxide paste: 2% of benzoyl peroxide are dissolved in a mixture of 70 parts of monomer from (1.) and 30 parts of triethylene glycol dimethylacrylate. 10 g of silanised glass ceramics are processed with 4 g of this solution to give a paste.

Amine paste: 1.3% of N-methyl-N-β-(methylcarbamoyloxy)-propyl-3,5-dimethylaniline are dissolved in a mixture of 70 parts of (1.a) and 30 parts of triethylene glycol dimethylacrylate. 4 g of this solution are processed with 10 g of silanised glass ceramics to give a paste.

If equal parts af amine paste and peroxide paste are mixed with one another, the mixture cures in 2 minutes. The pastes can be coloured with pigments and are suitable for filling dental cavities.

(b) Light-curing system 0.5% of N,N-diallyl-p-dimethylaminobenzenesulphonamide, 0.2% of camphor quinone and 0.125% of benzil dimethyl ketal are dissolved in a mixture of 70 parts of monomer from (1.) and 30 parts of triethylene glycol dimethacrylate. 10 g of silanised glass ceramics are processed with 4 g of this solution to give a paste. If this composition is irradiated with a commercial dental lamp (Translux, made by Kulzer), a layer of 7 mm is completely cured after 40 seconds.

7. Preparation of sealer solutions:

(a) Redox-curing system

Catalyst solution: 2% of benzoyl peroxide are dissolved in a mixture of 10 parts of triethylene glycol dimethacrylate and 90 parts of monomer (2).

Activator solution: 2.15% of N-methyl-N-β-(methylcarbamoyloxy)-propyl-3,5-dimethylaniline are dissolved in a mixture of 10 parts of triethylene glycol dimetharcylate and 90 parts of monomer (2).

A mixture of equal parts of catalyst solution and activator solution cures in 1 minute.

(b) Light-curing sealer 0.5% of N,N-diallyl-p-dimethylaminobenzenesulphonamide, 0.2% of camphor quinone and 0.125% of benzil dimethylketal are dissolved in a mixture of 30 parts of triethylene glycol dimethacrylate and 70 parts of monomer (3).

When irradiated with a commercial dental lamp (Translux made by Kulzer), the liquid cures to give a solid film.

We claim:

1. A (meth)-acrylic acid derivative of a tricyclodecane of the formula

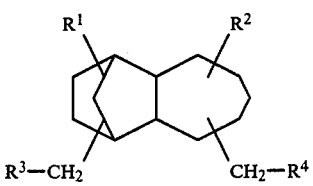

in which
R$^1$ and R$^2$ are identical or different and denote hydrogen, lower alkyl, lower alkoxy, halogen or trifluoromethyl and
R$^3$ and R$^4$ are identical or different and represent the groups

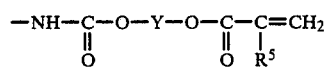

or

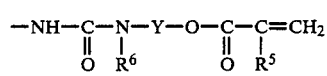

in which
Y is selected from the group consisting of a linear or branched hydrocarbon chain which has 2 to 10 carbon atoms, a linear or branched hydrocarbon chain which has 2 to 10 carbon atoms and contains at least one oxygen bridge, a linear or branched hydrocarbon chain which has 2 to 10 carbon atoms and is substituted by 1 to 4 acrylate or methacrylate radicals, and a linear or branched hydrocarbon chain which has 2 to 10 carbon atoms and contains at least one oxygen and is substituted by 1 to 4 acrylate or methacrylate radicals and
R$^5$ represents hydrogen or methyl and
R$^6$ represents hydrogen, lower alkyl or phenyl.

2. A (Meth)-acrylic acid derivative of a tricyclodecane according to claim 1,
wherein
R$^1$ and R$^2$ denote hydrogen,
R$^3$ and R$^4$ are identical or different and represent the group

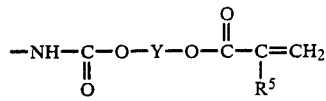

in which
Y is a linear or branched hydrocarbon chain which has 2 to 10 carbon atoms and can optionally contain 1 to 3 oxygen bridges and can optionally be substituted by 1 to 4 acrylate or methacrylate radicals, and
R$^5$ represents hydrogen or methyl.

3. A process for the the preparation of a (meth)-acrylic acid derivative of a tricyclodecane, wherein a diisocyanatomethyltricylodecane of the formula

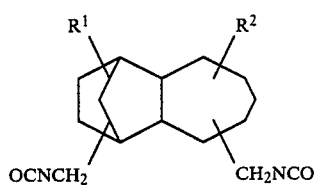

in which R$^1$ and R$^2$ are identical or different and denote hydrogen, lower alkyl, lower alkoxy, halogen or trifluoromethyl,
is reacted in the presence of a catalyst within the temperature range from 0° to 100° C., with a (meth)-acrylic acid derivative of

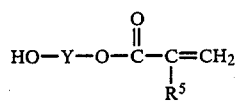

or

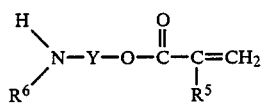

in which
Y is a linear or branched hydrocarbon chain which has 2 to 10 caron atoms, a linear or branched hydrocarbon chain which has 2 to 10 carbon atoms and contains at least one oxygen bridge, a linear or branched hydrocarbon chain which has 2 to 10 carbon atoms and is substituted by 1 to 4 acrylate or methacrylate radicals, and a linear or branched hydrocarbon chain which has 2 to 10 carbon atoms and contains at least one oxygen bridge and is substituted by 1 to 4 acrylate or methacrylate radicals and
R$^5$ represents hydrogen or methyl and
R$^6$ represents hydrogen, lower alkyl or phenyl.

4. A polymer formed from (meth)-acrylic acid derivatives of tricyclodecanes of the formula

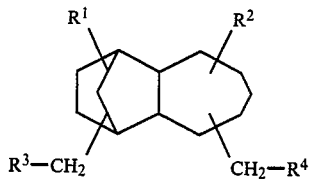

in which
R¹ and R² are identical or different and denote hydrogen, lower alkyl, lower alkoxy, halogen or trifluoromethyl and
R³ and R⁴ are identical or different and represent the groups

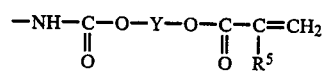

or

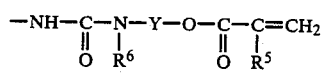

in which
Y is selected from the group consisting of a linear or branched hydrocarbon chain which has 2 to 10 carbon atoms, a linear or branched hydrocarbon chain which has 2 to 10 carbon atoms and contains at least one oxygen bridge, a linear or branched hydrocarbon chain which has 2 to 10 carbon atoms and is substituted by 1 to 4 acrylate or methacrylate radicals, and a linear or branched hydrocarbon chain which has 2 to 10 carbon atoms and contains at least one oxygen and is substituted by 1 to 4 acrylate or methacrylate radicals and
R⁵ represents hydrogen or methyl and
R⁶ represents hydrogen, lower alkyl or phenyl.

5. A tooth-filling composition comprising (meth)-acrylic acid derivatives of tricyclodecanes of the formula

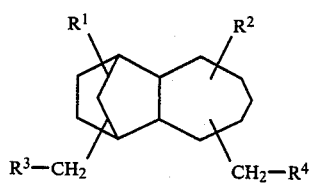

in which
R¹ and R² are identical or different and denote hydrogen, lower alkyl, lower alkoxy, halogen or trifluoromethyl and
R³ and R⁴ are identical or different and represent the groups

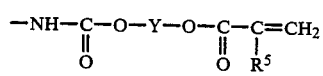

or

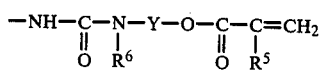

in which
Y is selected from the group consisting of a linear or branched hydrocarbon chain which has 2 to 10 carbon atoms, a linear or branched hydrocarbon chain which has 2 to 10 carbon atoms and contains at least one oxygen bridge, a linear or branched hydrocarbon chain which has 2 to 10 carbon atoms and is substituted by 1 to 4 acrylate or methacrylate radicals, and a linear or branched hydrocarbon chain which has 2 to 10 carbon atoms and contains at least one oxygen and is substituted by 1 to 4 acrylate or methacrylate radicals and
R⁵ represents hydrogen or methyl and
R⁶ represents hydrogen, lower alkyl or phenyl and 5 to 85% by weight of a suitable filler.

6. A tooth-filling compositions according to claim 5, comprising further comonomer in addition to a (meth)-acrylic acid derivative of tricyclodecanes.

7. A tooth coating composition comprising (meth)-acrylic acid derivatives of tricyclodecanes of the formula

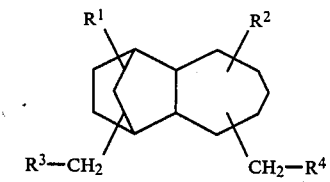

in which
R¹ and R² are identical or different and denote hydrogen, lower alkyl, lower alkoxy, halogen or trifluoromethyl and
R³ and R⁴ are identical or different and represent the groups

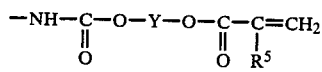

or

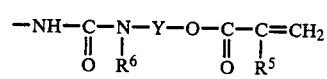

in which
Y is selected from the group consisting of a linear or branched hydrocarbon chain which has 2 to 10 carbon atoms, a linear or branched hydrocarbon chain which has 2 to 10 carbon atoms and contains at least one oxygen bridge, a linear or branched hydrocarbon chain which has 2 to 10 carbon atoms and is substituted by 1 to 4 acrylate or methacrylate radicals, and a linear or branched hydrocarbon chain which has 2 to 10 carbon atoms and contains at least one oxygen and is substituted by 1 to 4 acrylate or methacrylate radicals and
R⁵ represents hydrogen or methyl and
R⁶ represnets hydrogen, lower alkyl or phenyl.

8. A (meth)-acrylic acid derivative of a tricyclodecane according to claim 1 selected from the group consisting of

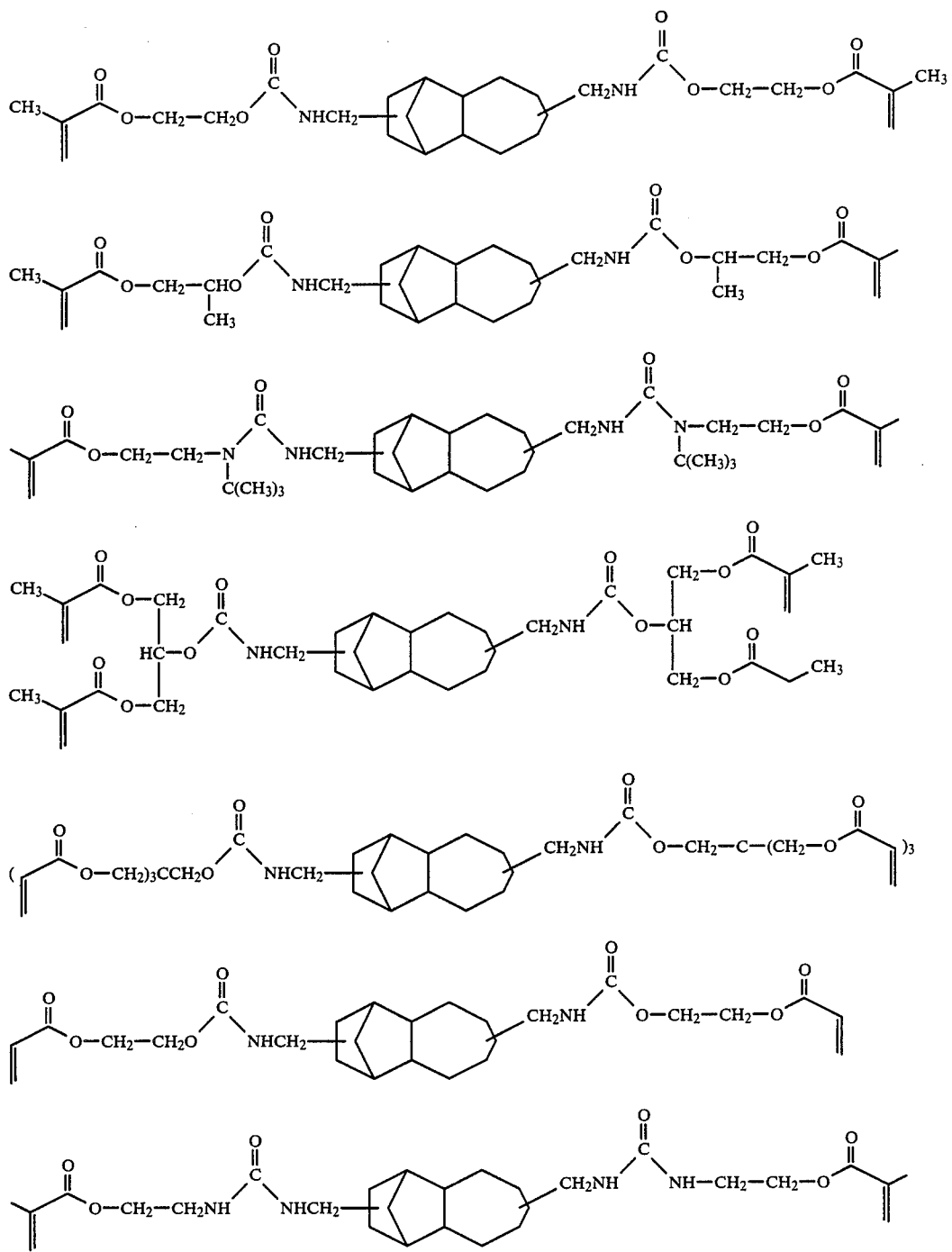
and
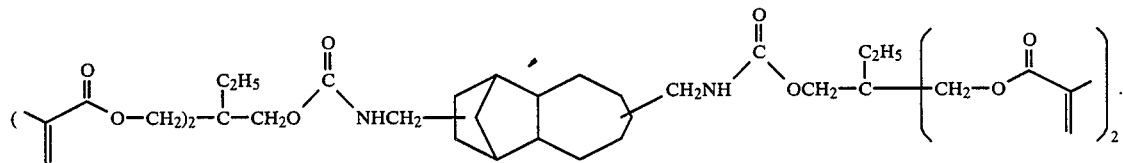
9. A process according to claim 5, wherein the reaction is carried out in the presence of an inert solvent.

UNITED STATES PATENT AND TRADEMARK OFFICE
CERTIFICATE OF CORRECTION

PATENT NO. : 4,744,828  Page 1 of 2
DATED : May 17, 1988
INVENTOR(S) : Jens Winkel, et al.

It is certified that error appears in the above-identified patent and that said Letters Patent is hereby corrected as shown below:  Title page:

| | |
|---|---|
| Title Page, "Abstract", | Line 7, after "groups" delete "."; line 17, delete "represent" and substitute --represents-- |
| Col. 1, line 35 | After "R$^3$" insert --and-- |
| Col. 2, line 63 | Before "hydroxy" delete "of" and substitute --and-- |
| Col. 6, line 64 | Delete "[2'" and substitute --[p-(2'-- |
| Col. 7, line 31 | Correct spelling of --phenanthrenequinone-- |
| Col. 8, line 1 | After "fillers" delete "to" and substitute --into-- |
| Col. 8, lines 6-7 | Correct --lanthanum-- |
| Col. 9, line 58 | Delete "H-NMR" and substitute --$^1$H-NMR-- |
| Col. 10, line 48 | Delete "curving" and substitute --curing-- |
| Col. 10, line 49 | Delete "peroxide" and substitute --Peroxide-- |
| Col. 10, line 60 | Delete "af" and substitute --of-- |
| Col. 11, line 15 | Correct spelling of --dimethacrylate-- |
| Col. 12, line 21 | Delete "the" second instance |
| Col. 12, line 23 | Correct spelling of --diisocyanatomethyltricyclodecane-- |
| Col. 12, line 54 | Delete "caron" and substitute --carbon-- |
| Col. 14 line 17 | Delete "compositions" and substitute --composition-- |

UNITED STATES PATENT AND TRADEMARK OFFICE
CERTIFICATE OF CORRECTION

PATENT NO. : 4,744,828

DATED : May 17, 1988

INVENTOR(S) : Jens Winkel, et al

It is certified that error appears in the above-identified patent and that said Letters Patent is hereby corrected as shown below:

Col. 14, line 64    Correct spelling of --represents--
Col. 16, line 63    Delete "claim 5" and substitute --claim 3--

Signed and Sealed this

Twenty-fourth Day of January, 1989

Attest:

DONALD J. QUIGG

Attesting Officer    Commissioner of Patents and Trademarks

UNITED STATES PATENT AND TRADEMARK OFFICE
CERTIFICATE OF CORRECTION

PATENT NO. : 4,744,828

DATED : May 17, 1988

INVENTOR(S) : Jens Winkel, et al

It is certified that error appears in the above-identified patent and that said Letters Patent is hereby corrected as shown below:

Abstract, line 3; Col. 1, line 25; Cols. 3-4, Middle of each of 8 formula; Col. 5, line 1; Col. 9, Table 1, each of 4 formulas; Col. 11, line 33; Col. 12, line 30; Col. 13, line 5; Col. 13, line 48; Col. 14, line 27, Cols. 15-16, middle of each of 8 formulas Delete seven-membered ring in formula and substitute:

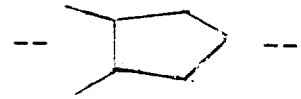

Signed and Sealed this

Sixth Day of June, 1989

Attest:

DONALD J. QUIGG

Attesting Officer

Commissioner of Patents and Trademarks